(12) United States Patent
Lundell et al.

(10) Patent No.: US 6,611,780 B2
(45) Date of Patent: *Aug. 26, 2003

(54) SYSTEM FOR COMMUNICATING OPERATIONAL DATA BETWEEN AN ELECTRIC TOOTHBRUSH AND A SEPARATE CONTROL UNIT

(75) Inventors: William G. Lundell, Issaquah, WA (US); David Bayeh, Seattle, WA (US)

(73) Assignee: Koninklijke Philips Electronics N.V., Eindhoven (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/329,007

(22) Filed: Jun. 9, 1999

(65) Prior Publication Data

US 2002/0133308 A1 Sep. 19, 2002

(51) Int. Cl.[7] .................................................. A61C 3/00
(52) U.S. Cl. ......................................... 702/122; 437/27
(58) Field of Search ........................... 702/122; 433/27; 15/22.1, 22.2; 60/162; 340/870.01, 570.28, 870.29

(56) References Cited

U.S. PATENT DOCUMENTS

| | | | | | |
|---|---|---|---|---|---|
| 5,544,382 | A | * | 8/1996 | Giuliani et al. | 15/22.1 |
| 5,561,881 | A | * | 10/1996 | Klinger et al. | 15/22.1 |
| 5,734,254 | A | * | 3/1998 | Stephens | 320/106 |
| 5,784,742 | A | * | 7/1998 | Giuliani et al. | 15/22.1 |
| 5,894,670 | A | * | 4/1999 | Iso et al. | 30/541 |
| 5,959,287 | A | * | 9/1999 | Myers et al. | 235/472.02 |
| 6,094,642 | A | * | 7/2000 | Stephenson et al. | 705/28 |
| 6,102,284 | A | * | 8/2000 | Myers et al. | 235/375 |
| 6,140,802 | A | * | 10/2000 | Lundell et al. | 320/136 |

* cited by examiner

*Primary Examiner*—Patrick Assouad
(74) *Attorney, Agent, or Firm*—Ernestine C. Bartlett

(57) ABSTRACT

A system for communicating data between a battery powered electric toothbrush and a separate control unit includes a microprocessor in the toothbrush which collects and stores data concerning selected operational aspects of the toothbrush. The data is transmitted from the toothbrush to the control unit by means of an infrared link. The transmitted data is processed in the control unit and displayed there or is transmitted to a separate device for display and/or analysis.

23 Claims, 5 Drawing Sheets

SYSTEM FOR COMMUNICATING OPERATIONAL DATA BETWEEN AN ELECTRIC TOOTHBRUSH AND A SEPARATE CONTROL UNIT

TECHNICAL FIELD

This invention relates generally to battery powered electric toothbrushes, and more specifically concerns a toothbrush which is capable of providing information concerning use of the toothbrush to a separate control unit which in turn can display or analyze the information or transmit it to another device.

BACKGROUND OF THE INVENTION

Both manual and power toothbrushes operate in various ways to produce a cleansing effect on the teeth of the user. A few toothbrushes attempt to provide specific information to the user concerning operation of the toothbrush during use. In many cases, this information is an indication of desired or actual brushing times. In other cases, information is provided concerning pressure applied by the user on the brush against the teeth, with the pressure being determined in various ways and then displayed or otherwise communicated to the user. However, any information displayed on the toothbrush itself is typically difficult for the user to read and further, in many cases, there is insufficient room for an adequate display of any information. Toothbrushes which supply information to the user, particularly in the form of a display, are thus relatively rare and usually ineffective. Still further, toothbrushes which supply information to persons other than the user, such as for analysis of brushing use, are unknown.

In the past, toothbrushes have not accumulated any information relative to their use/non-use. Further, other information concerning the operating condition of the toothbrush, such as the state of the battery or other structural information has not been available from the toothbrush. Clinical trials of new toothbrush configurations could become much more reliable if such information were available.

Actual usage information could be helpful to the user in maintaining good brushing technique; usage information could also be accumulated and used to monitor patient compliance against established guidelines. Analysis of actual recorded data is typically much more reliable than a patient's memory relative to brush use.

Hence, it would be desirable for a toothbrush or similar device to have the capability of accumulating actual use and/or operating condition information and then to transmit that information to another device for display and/or analysis.

SUMMARY OF THE INVENTION

Accordingly, the present invention is a system for communicating data between an electric toothbrush or other instrument and a separate control unit, comprising: means in the electric toothbrush for collecting and storing data concerning operation of the electric toothbrush; means for transmitting the data to a receiving member in the control unit when the toothbrush is present in the control unit; and means for displaying or analyzing the transmitted data.

BEST MODE FOR CARRYING OUT THE INVENTION

Figure 1:
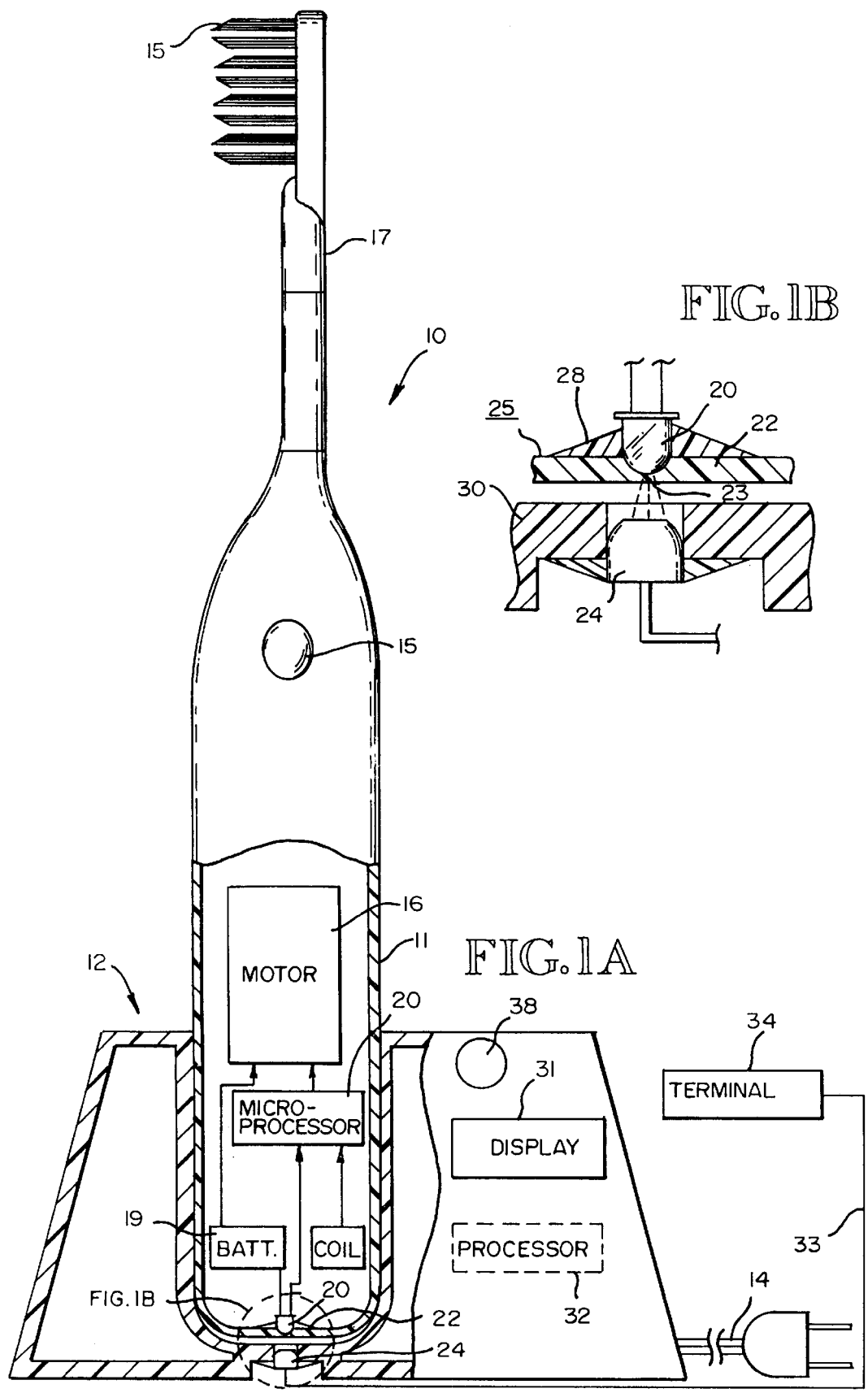
FIGS. 1A and 1B are diagrams showing a power toothbrush combination comprising a battery-powered toothbrush and a control unit which embody the present invention.

FIGS. 1A and 1B show one specific embodiment of the present invention, specifically a battery-powered electric toothbrush 10, which includes a handle portion 11, which in turn can fit into a control unit 12. The terms control unit and control base used herein refer to both a base unit which does not have a battery charging capability, as well as a base unit which does have a battery charging capability. The toothbrush 10 could have a separate charging unit which has the capability of charging the battery. The control unit could be separate from the charging unit or the functions of the control unit could be incorporated into the charging unit. Control unit 12 is connected to the wall by means of a power cord and plug 14. In the embodiment shown, toothbrush 10 includes a brushhead 15 which is mounted on a lever arm 17. The lever arm is in turn vibrated about a pivot by means of an electromagnetic motor 16 contained within handle 11. Motor 16 is in turn powered by a battery 18.

Battery 18 in the embodiment shown can be charged through an inductive coil arrangement (not shown) between a charging base unit and toothbrush 10. Such an inductive arrangement results in the battery being charged without any direct connection between the charging unit and the battery. Such an arrangement is described in U.S. Pat. No. 5,796,325, owned by the assignee of the present invention, the contents of which are incorporated by reference herein.

In use, toothbrush 10 is simply lifted out of such a charging unit, which may or may not contain the elements of control unit 12, and turned on by means of a switch on the toothbrush, such as pushbutton switch 15. In the present invention, usage and operational data for toothbrush 10 is accumulated by a microprocessor controller 19 present in toothbrush 10. While the present invention is described relative to the particular embodiment of FIGS. 1A and 1B, it should be understood that the invention can be used in other toothbrush arrangements and configurations and even in other battery-powered tools or instruments, where usage and operational information is important. Some examples of such other tools and/or instruments are electric shavers, electric tools such as drills, or other electric devices, such as massagers, electronic cameras and cell phones.

Data transmission between toothbrush 10, which records and accumulates the usage and operation data, and the control base 12 is achieved in a wireless manner through infrared transmission in the embodiment shown. Such an arrangement is shown in FIGS. 1A and 1B. As indicated above, this control base capability would be included in a charging base unit, or more typically, in a separate base unit. The control unit will typically, but not necessarily, be located in a separate facility from the place of use of the toothbrush, such as a dental office or research laboratory. The information will be of primary interest to dental health personnel or research personnel, although it could certainly be helpful to the user directly as well. It is also possible to transmit the information accumulated by the control unit to other facilities for analysis or display, from a control unit located in the normal place of use. More typically, however, the user will bring the toothbrush to the separate facility for information transfer.

As indicated above, data concerning the use and operation of the toothbrush is accumulated and then stored in control microprocessor 19. That information is then transmitted to an infrared LED 20 which is positioned adjacent bottom wall portion 22 of toothbrush 10, in response to an initiating signal. A small part 23 of bottom wall portion 22 of the toothbrush is relatively thin (approximately 0.01 inches thick) so that infrared light can be transmitted therethrough. LED 20 is sealed to the inner surface 25 of thin part 23 with a layer section of epoxy 28. The epoxy layer 28 provides the necessary thickness and strength to thin part 23 so as to maintain a structurally sound bottom portion of toothbrush 10.

An infrared detector (phototransistor) 24 is positioned in a base portion 30 of control unit 12 (FIG. 1B), arranged so that it is physically aligned with infrared LED 20 when the toothbrush 10 is properly positioned in the control base. Data accumulated by microprocessor 19 is transmitted via the infrared LED/phototransistor combination into a memory 32 in control unit 12. The stored data can then either be displayed at the control unit itself, such as through display 31, or it can be transmitted via a communication link 33 to a separate device 34, which could be a stand-alone display, or even a computer for analyzing the information.

In general, it is important that data communication between the toothbrush and the control unit 12 be wireless. This allows the toothbrush to separate completely from the control unit in use. Infrared communication is one example of wireless communication. Other arrangements of wireless communication could be used. One example is an inductive system, using matching coils. Still another example of a wireless system is radio frequency transmission.

Generally, communication of data from the toothbrush to control unit 12 will occur in the following sequence. The transfer of information from the toothbrush handle or other battery-powered device is initiated by pushing a start button on the toothbrush itself, or a button 38 on the control base 12. This could be done by the actual user of the device or by other personnel. The microprocessor 19 in the toothbrush 10 can be programmed to recognize either or both possibilities. The microprocessor 19 will recognize a start button being operated when the toothbrush is still in the control base and will commence sending data. Alternatively, the microprocessor will recognize a predetermined data string transmitted from the control base 12 when a switch present in the control base is operated. Upon recognition of a proper initiate sequence, the microprocessor will commence sending the data stream to the LED 20 in the handle 11 of the toothbrush.

Typically, the data stream from the toothbrush will consist of a serial transmission of ones and zeros. The present invention uses short and long pulses to the data. For a data "one" pulse, the timing of the transmitted pulse, i.e. its duty cycle, will be at least $\frac{2}{3}$ of the entire bit time period, while for "zero", the pulse will be less than $\frac{1}{3}$ of the bit time period. This is just one example of a possible data transmission code. It should thus be understood that other timing arrangements can be used.

In the embodiment shown, the transmission of the data is followed by a checksum value to insure that correct data is received by the control base 12 from toothbrush 10. In the embodiment shown, however, the data is not automatically resent if there is an error in transmission. If the check sum indicates that bad data was received, the user can simply press the start button on the toothbrush handle or the charger to initiate another transmission of the data, because the data is not cleared from the memory of the microprocessor in the toothbrush upon transmission, i.e. the data is preserved in memory. Counters having a sufficient capacity are provided in the toothbrush microprocessor 19 to accommodate the data. The counters in operation count through zero during data accumulation.

The data collection unit in the toothbrush maintains previous data readings as a boundary or offset relative to the particular data being transmitted. Data can thus not be inadvertently cleared from the microprocessor memory in the toothbrush.

After the data is received by the control base through the infrared LED and phototransistor combination, the resulting electrical signals from the phototransistor are provided to a processing unit 32 in the control base 12. The processor 32 decodes the ones and zeros comprising the data based on the particular duty cycle principles used to encode the data in the toothbrush. The processor then uses the data checksum at the end of the transmission to determine whether the data sent is correct. If the data is fact valid, it is displayed on display 30 in the control base or transmitted to another device 34.

Figure 2:
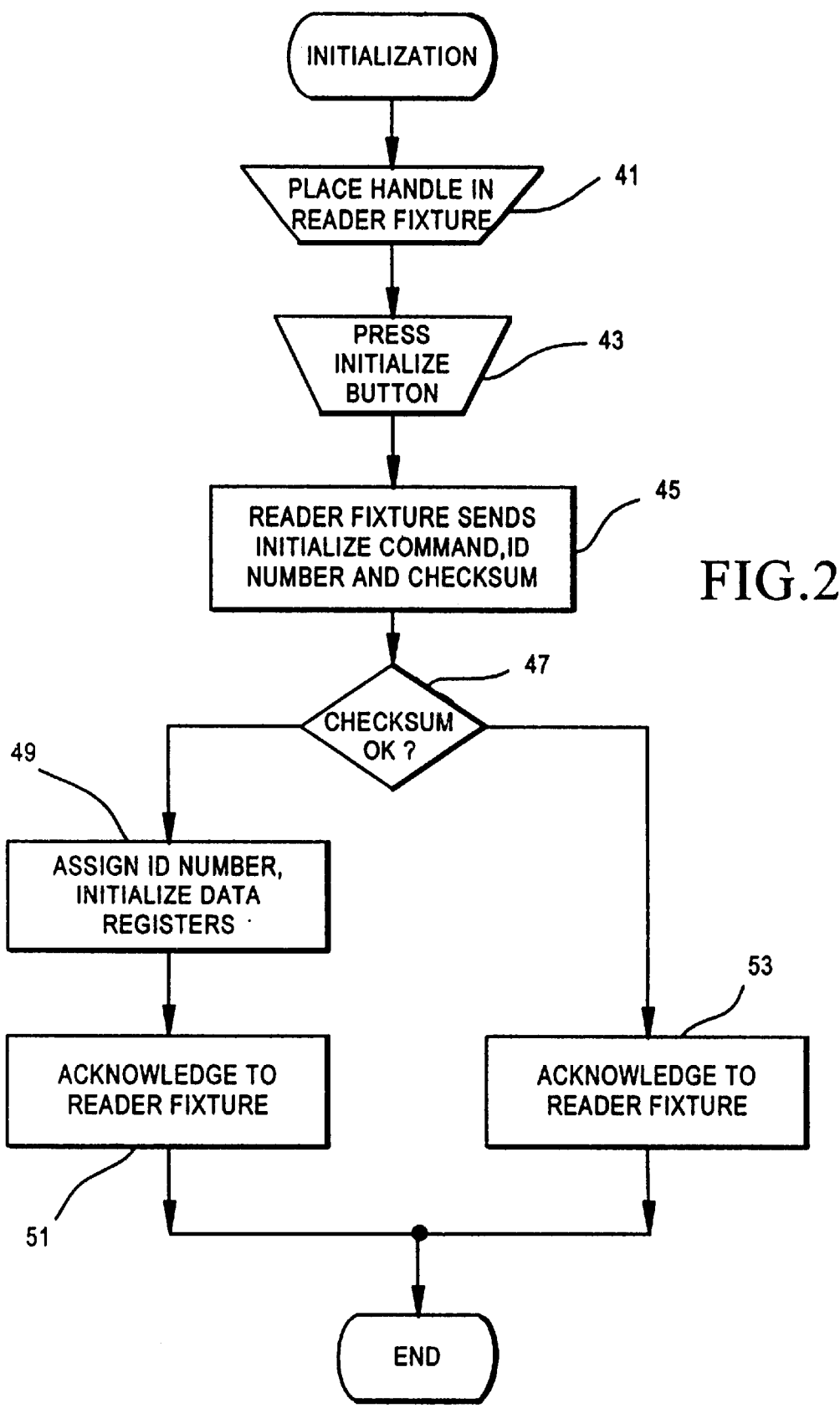
FIG. 2 is a flow chart diagram for the initialization of the toothbrush of FIG. 1.

FIG. 2 shows initialization steps for toothbrush 10 during the manufacturing process. At block 41, the toothbrush is placed in a fixture at the manufacturing facility. An initialize button on the fixture is then operated, as shown at block 43. The fixture then transmits an initialize command, an ID number and checksum, in the form of a series of pulses, to the toothbrush, as shown at block 45. This is done inductively in the embodiment shown, from a coil in the fixture into coil 44 in the toothbrush. Coil 44 also serves as a charging coil in normal use of the toothbrush.

The pulses picked up by coil 44 in the toothbrush are then applied to the charge pin of the microprocessor. At block 47, the toothbrush microprocessor recognizes the initialize command and if the checksum is correct, assigns the transmitted ID number to the toothbrush and clears all the data registers in the toothbrush microprocessor, as shown at block 49. The toothbrush now has an identification number to identify the data it will later transmit. The toothbrush microprocessor then sends an acknowledgment back through the coil 44 to the control base, as shown at block 51. As shown at block 53, if the checksum is incorrect, the toothbrush will send back a different acknowledgment indicating incorrect data. The initializing information could of course be provided in other ways, such as infrared transmission, or directly to the microprocessor, either prior to final assembly or through an access opening.

Figure 3:
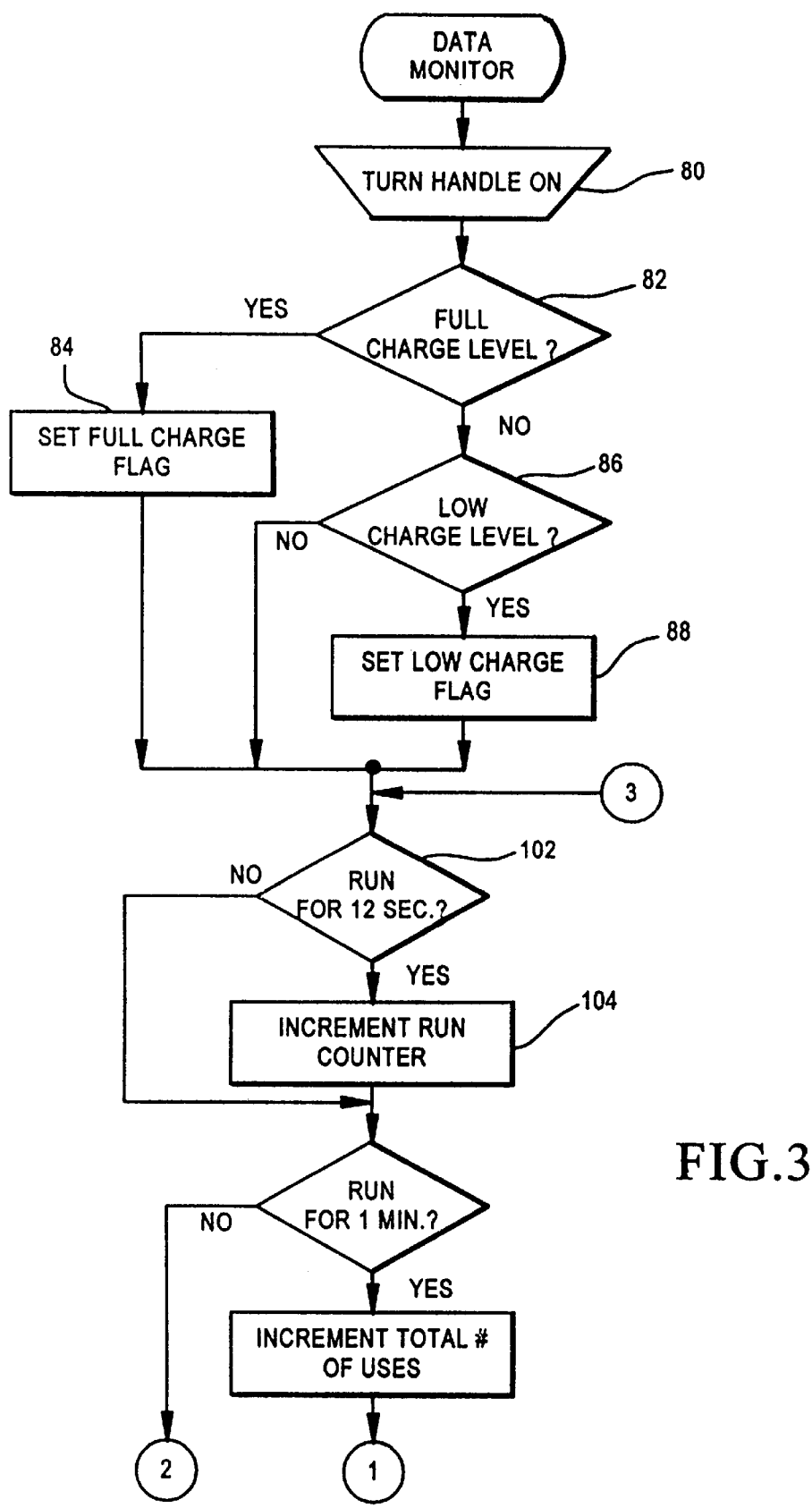
FIGS. 3 and 4 are flow chart diagrams showing the collection of data in the toothbrush of FIG. 1.
Figure 4:
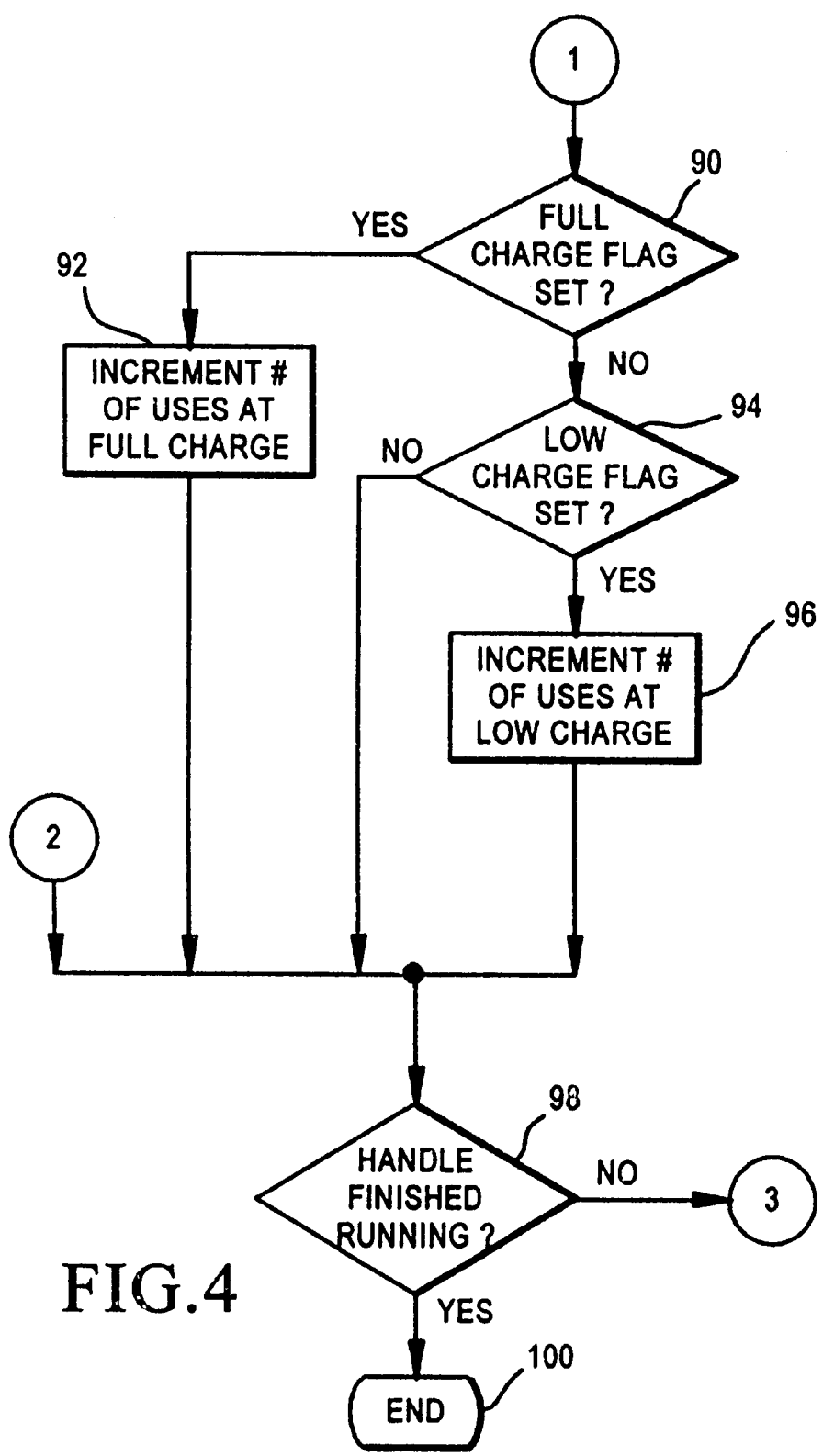

FIGS. 3 and 4 show the steps in the collection of the use/operation data for the embodiment shown. In block 80, the toothbrush is turned on in normal use, i.e. the toothbrush is lifted from a charging base unit and the start button on the toothbrush is pushed. At this point, the charge level of the battery in the toothbrush is checked at block 82 to determine whether it is at a predetermined full charge level. If it is, a full charge flag is set at block 84. On the other hand, if the battery is not at full charge, then the battery is checked to determine whether or not the battery is below a predetermined low battery value, at block 86. If it is, a low charge flag is set at block 88.

Next, at block at 102, the time of use of the toothbrush is determined, for twelve second successive intervals. For each successive twelve second period that the toothbrush runs, a run counter is incremented, at block 104. When the toothbrush stops (the "no" branch from block 102) or if the toothbrush is still running and the run counter is incremented, a determination is then made, at block 106, whether or not the toothbrush has been running for a minimum of one minute. If yes, then the total number of uses counter is incremented, at block 108. If no, then a determination is made whether the handle has finished running, at block 98 (FIG. 4). If the decision from block 98 is yes, then the routine ends, at block 100. If the decision is no, the program doubles back to block 102.

The incrementing of the total number of uses counter in block 108 leads to a subroutine (FIG. 4) in which the program checks to see if the full charge flag is set at that point in time, at block 90. If it is, then a number of uses counter at full charge is incremented, at block 92. If the full charge flag is not set, then the program checks to see if the low charge flag is set at that point in time, at block 94. If it is, then the counter for low charge uses is incremented, at block 96. The incrementing of the full charge uses counter and low charge uses counter leads to block 98, for a determination of whether the toothbrush is finished running. If yes, the data collection program terminates at 100. If not, the program doubles back to block 102.

Figure 5:
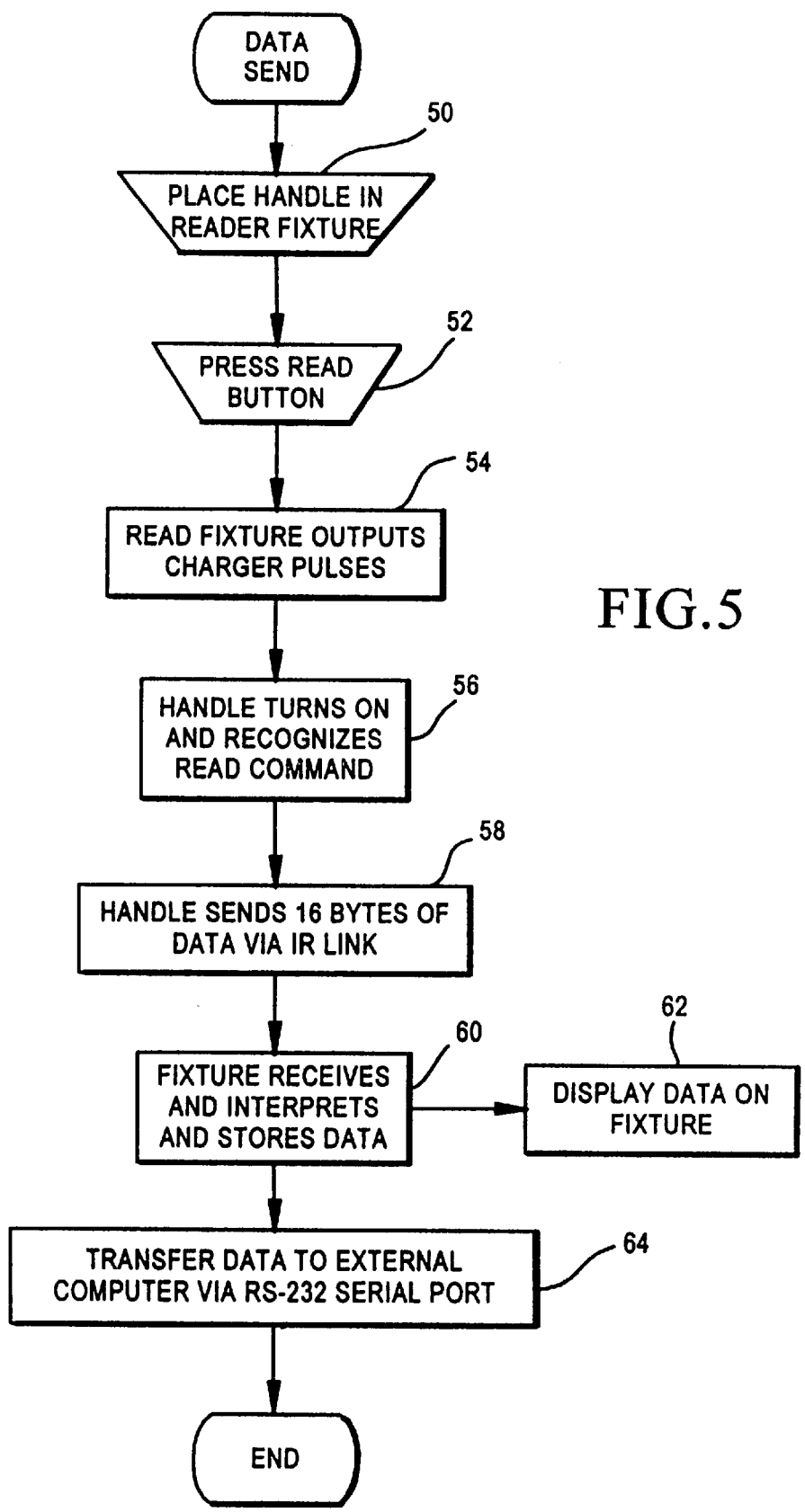
FIG. 5 is a flow chart showing the control steps for transferring data from the toothbrush to the control unit shown in FIG. 1.

FIG. 5 shows the program sequence for data transmission. Referring to FIG. 5, in block 50, the toothbrush (handle) is positioned in the control base (the reader fixture) so that the infrared LED in the handle is lined up with the infrared phototransistor in the control base. Again, the control unit (base) could be a completely separate device which may be located at a clinic or research facility, or it could be part of a charger base at the location of the toothbrush.

In block 52, a "read" button on the control base is activated. The control base at block 54 initiates action of the microprocessor in the toothbrush. In another embodiment, a start button on the toothbrush could be used to initiate action.

When the toothbrush 10 is activated by the control unit, the toothbrush will recognize the "read" pattern produced by the control base, at block 56, and in response, at block 58, the toothbrush transmits 18 bytes of use/operation data. The control base, at block 60, receives, processes and stores the transmitted data, and either displays the data at the base, as shown at block 62, or transmits the data via a serial port to an external computer or other terminal for display and/or analysis or other processing, as shown at block 64.

This completes the operation of the unit. While the transmitted data is primarily toothbrush use data transmitted from the toothbrush to the control unit, it should be noted that selected information, including possibly programming information for the toothbrush, can be transmitted from the control base to the toothbrush. As used with toothbrushes, the present invention has a number of possible advantages, including, among others, the recording of actual use patterns of the toothbrush. Actual use can be substantially different than a user's recollection of use. The present invention is capable of providing accurate and complete data relative to actual use, such as brushing times, as well as operating condition of the toothbrush, such as battery power level.

The above-described system can be used to effectively analyze abnormal results of brushing or to verify actual user profiles in clinical situations. Still further, the present invention can be used to monitor and control use of the toothbrush by particular patients. For instance, the displayed information can be used by a person overseeing use of the toothbrush, such as a parent or a dentist. Still further, clinical studies can be more quickly advanced because differences in use of a toothbrush, i.e. multiple types of use, can be automatically tracked without having to reprogram the toothbrush between each use. Accurate comparison data thus can be readily obtained and analyzed.

Thus, the transmitted information can be simply displayed and reviewed, by the user or a practitioner, with possible feedback to the user, or can be analyzed, including analysis by a computer program, to determine usage patterns, brushing effectiveness or to address other research questions.

Hence, a system has been described for communicating data in a wireless fashion between a toothbrush or similar device and a separate control base. Such a system is quite significant in that it provides actual use and operation data, which can assist in the study of various types of toothbrush use, as well as monitoring compliance. It should be understood that a wide variety of data can be obtained and transmitted, beyond the actual use times and battery condition data specifically discussed. The term "operation data" used herein is intended to have a broad meaning including actual use information and other information, such as battery condition, which related to the operation of the device. Further, while the invention has been disclosed in the context of a power toothbrush, other tools/instruments could use the system as well. Several examples were provided above.

Thus, a preferred embodiment of the invention has been disclosed for purposes of illustration. However, it should be understood that various changes, modifications and substitutions could be made in the preferred embodiment without departing from the spirit of the invention, which is defined by the claims which follow:

What is claimed is:

1. A system for communicating data between an electric toothbrush and a separate control unit, comprising:

means in the electric toothbrush for collecting and storing data concerning operation of the electric toothbrush;

means for transmitting the data to a receiving member in the control unit when the toothbrush is present in the control unit, wherein the toothbrush is removable from the control unit;

storing means located in the control unit for storing the transmitted data from the toothbrush, including means for collecting and storing the data transmitted from the toothbrush over a period of time covering a plurality of uses of the electric toothbrush; and means for accomplishing at least one of the following:
(a) displaying the transmitted and stored data and (b) analyzing the transmitted and stored data.

2. A system of claim 1, wherein the displaying means is located in the control unit.

3. A system of claim 1, wherein the displaying means is separate from the control unit and wherein the system includes a communication link between the control unit and the displaying means.

4. A system of claim 1, wherein the control unit includes means for charging a battery in the toothbrush, the battery providing power for the toothbrush.

5. A system of claim 1, wherein the communication of data between the toothbrush and the control unit is wireless.

6. A system of claim 1, including means for validating the accuracy of the data transmitted from the toothbrush to the control unit.

7. A system of claim 1, wherein the transmitted data includes information concerning use of the toothbrush.

8. A system of claim 1, wherein the transmitted data includes information concerning the charge level of a battery in the toothbrush.

9. A system for communicating data between a battery powered instrument and a separate control unit therefor, comprising:

means in the instrument for collecting and storing data concerning operation of the instrument;

means for transmitting the data to a receiving member in the control unit when the instrument is present in the control unit, wherein the instrument is removable from the control unit;

storing means located in the control unit for storing the transmitted data from the instrument, including means for collecting and storing the data transmitted from the instrument over a period of time covering a plurality of uses of the instrument; and means for accomplishing at least one of the following:
(a) displaying the transmitted and stored data and (b) analyzing the transmitted and stored data.

10. A system of claim 9, wherein the displaying means is located in the control unit.

11. A system of claim 9, wherein the displaying means is separate from the control unit and wherein the system includes a communication link between the control unit and the displaying means.

12. A system of claim 9, wherein the communication of data between the instrument and the control unit is wireless.

13. A system of claim 9, wherein the control unit includes means for charging a battery in the instrument, the battery providing power for the instrument.

14. A system for communicating data between an electric toothbrush and a separate control unit, comprising:

means in the electric toothbrush for collecting and storing data concerning operation of the electric toothbrush;

means for transmitting the data to a receiving member in the control unit when the toothbrush is in the control unit;

means for accomplishing at least one of the following:
(a) displaying the transmitted data and (b) analyzing the transmitted data; and means for transmitting programming information for program control of the electric toothbrush from the control unit to the electric toothbrush.

15. A system of claim 14, wherein the communication of data and information between the toothbrush and the control unit is wireless.

16. A system of claim 14, including means in the toothbrush for storing information transmitted by the control unit.

17. A system of claim 16, including means for validating the accuracy of the data transmitted from the toothbrush to the control unit.

18. A system of claim 16, wherein the transmitted data includes information concerning use of the toothbrush.

19. A system for communicating data between a battery powered instrument and a separate control unit, comprising:

means in the instrument for collecting and storing data concerning operation of the instrument;

means for transmitting the data to a receiving member in the control unit when the instrument is present in the control unit;

means for accomplishing at least one of the following:
(a) displaying the transmitting data and (b) analyzing the transmitted data; and means for transmitting programming information for program control of the instrument from the control unit to the instrument.

20. A system of claim 19, wherein the communication of data and information between the instrument and the control unit is wireless.

21. A system of claim 19, including means in the instrument for storing information transmitted by the control unit.

22. A system of claim 14, including means for validating the accuracy of the data transmitted from the instrument to the control unit.

23. A system of claim 19, wherein the transmitted data includes information concerning use of the instrument.

* * * * *

UNITED STATES PATENT AND TRADEMARK OFFICE
CERTIFICATE OF CORRECTION

PATENT NO. : 6,611,780 B2 Page 1 of 1
DATED : August 26, 2003
INVENTOR(S) : William G. Lundell and Daniel Bayeh It is certified that error appears in the above-identified patent and that said Letters Patent is hereby corrected as shown below:

Column 1,
Beginning at line 5, insert the following:
-- This invention was made with government support under Grant No. 5 R44 DE10455-036, awarded by the National Institute of Dental and Craniofacial Research. The government has certain rights in the invention. --

Signed and Sealed this

Twenty-fifth Day of November, 2003

JAMES E. ROGAN
*Director of the United States Patent and Trademark Office*